United States Patent
Kiyama et al.

(10) Patent No.: US 10,329,525 B2
(45) Date of Patent: *Jun. 25, 2019

(54) LIQUID FEEDING DEVICE AND CELL CULTURE DEVICE

(71) Applicant: Hitachi, Ltd., Tokyo (JP)

(72) Inventors: Masaharu Kiyama, Tokyo (JP); Guangbin Zhou, Tokyo (JP); Takayuki Nozaki, Tokyo (JP); Ryota Nakajima, Tokyo (JP); Daisuke Suzuki, Tokyo (JP); Yumiko Igarashi, Tokyo (JP); Shizu Takeda, Tokyo (JP); Taku Nakamura, Tokyo (JP); Masakazu Sugaya, Tokyo (JP); Koichi Terada, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 131 days.

This patent is subject to a terminal disclaimer.

(21) Appl. No.: 15/323,977

(22) PCT Filed: Jul. 23, 2014

(86) PCT No.: PCT/JP2014/069452
§ 371 (c)(1),
(2) Date: Jan. 5, 2017

(87) PCT Pub. No.: WO2016/013070
PCT Pub. Date: Jan. 28, 2016

(65) Prior Publication Data
US 2017/0198249 A1    Jul. 13, 2017

(51) Int. Cl.
*C12M 1/00* (2006.01)
*C12M 1/34* (2006.01)
*C12M 1/36* (2006.01)

(52) U.S. Cl.
CPC ............ *C12M 41/40* (2013.01); *C12M 23/14* (2013.01); *C12M 23/40* (2013.01); *C12M 29/00* (2013.01);
(Continued)

(58) Field of Classification Search
CPC ...... C12M 29/00; C12M 23/14; C12M 23/40; C12M 41/48; C12M 41/40; C12M 29/26; C12M 29/14
See application file for complete search history.

(56) References Cited

U.S. PATENT DOCUMENTS

2005/0118702 A1    6/2005    Erhardt et al.
2006/0115889 A1    6/2006    Nakashima et al.
(Continued)

FOREIGN PATENT DOCUMENTS

EP    2 832 847 A1    2/2015
EP    2 902 475 A1    8/2015
(Continued)

OTHER PUBLICATIONS

Extended European Search Report received in corresponding European Application No. 14898112.9 dated Feb. 19, 2018.
(Continued)

*Primary Examiner* — Gautam Prakash
(74) *Attorney, Agent, or Firm* — Mattingly & Malur, PC

(57) ABSTRACT

There is the problem that a liquid culture medium fed by a pump has a high frequency of contact with a gas during movement in a tube, and the pH value of the liquid culture medium before and after feeding changes easily. In a liquid feeder and a cell culture apparatus provided therewith, a feed pipe 7 is connected with a gas bag 14, the liquid to be fed into the feed pipe 7 is fed so as to be sandwiched by a gas for suppressing the qualitative changes of the liquid. Furthermore, the gas bag is connected with a container 8 for (Continued)

holding a liquid, and holds the gas for suppressing qualitative changes of the liquid in a gas phase of the container.

11 Claims, 3 Drawing Sheets

(52) U.S. Cl.
CPC ............ *C12M 29/14* (2013.01); *C12M 29/26* (2013.01); *C12M 41/48* (2013.01)

(56) References Cited

U.S. PATENT DOCUMENTS

| | | |
|---|---|---|
| 2007/0172945 A1 | 7/2007 | O'Kennedy et al. |
| 2010/0330547 A1 | 12/2010 | Tempelman et al. |
| 2015/0218503 A1* | 8/2015 | Kiyama .................. C12M 23/10 435/297.1 |

FOREIGN PATENT DOCUMENTS

| | | |
|---|---|---|
| EP | 3 037 516 A1 | 6/2016 |
| EP | 3 059 299 A1 | 8/2016 |
| JP | 08-108061 A | 4/1996 |
| JP | 2005-087114 A | 4/2005 |
| JP | 2006-149268 A | 6/2006 |
| JP | 2007-222120 A | 9/2007 |
| JP | 2007-535961 A | 12/2007 |
| JP | 2013-139442 A | 7/2013 |
| WO | 2014/049701 A1 | 4/2014 |

OTHER PUBLICATIONS

International Search Report of PCT/JP2014/069452 dated Sep. 22, 2014.

* cited by examiner

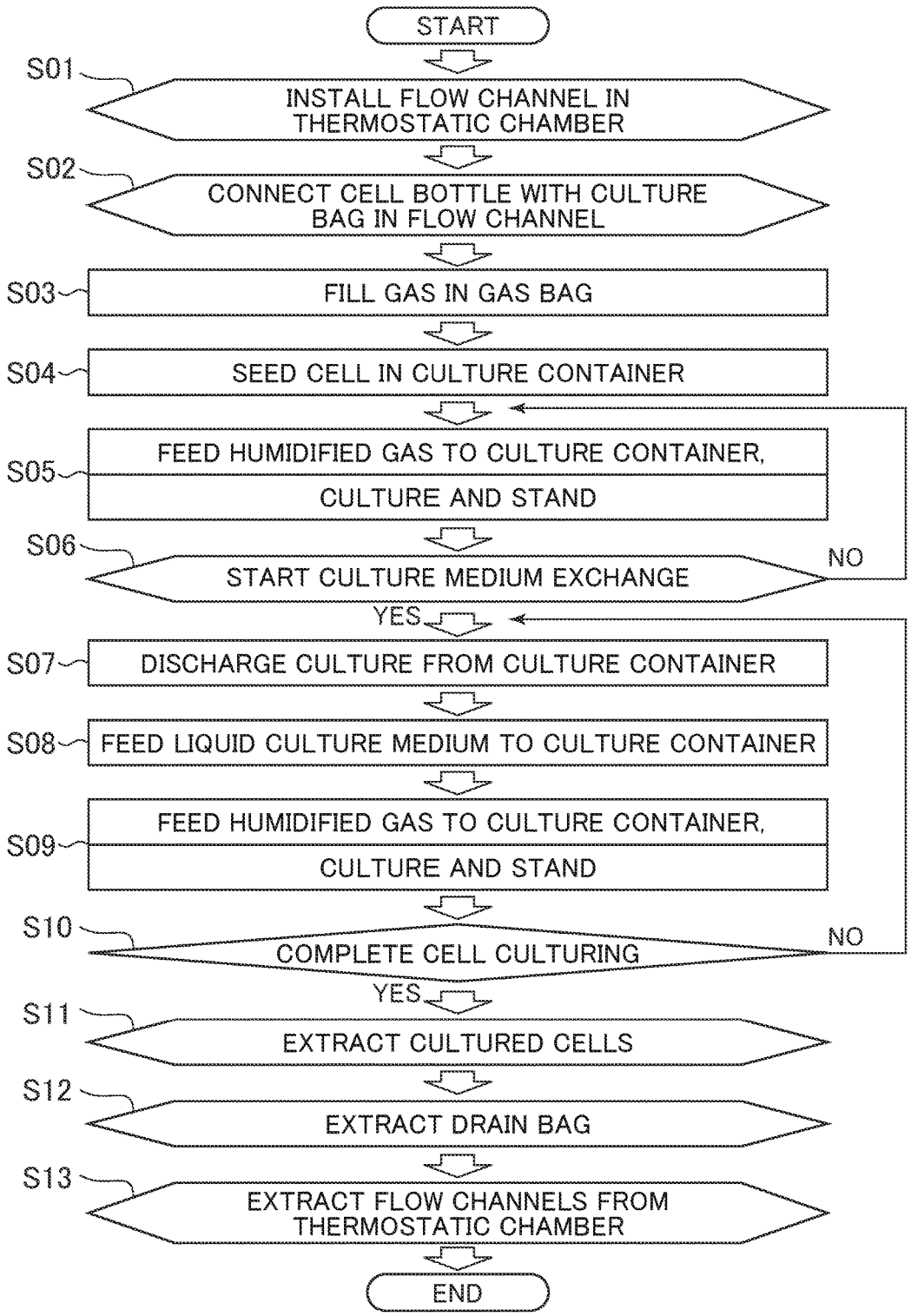

LIQUID FEEDING DEVICE AND CELL CULTURE DEVICE

TECHNICAL FIELD

The present invention relates to a cell culture apparatus for culturing cells, and specifically, relates to a liquid feeder technology such as for a liquid culture medium.

BACKGROUND ART

In regenerative medicine performed to treat diseases by using cells of patients themselves or others, cells collected from living bodies are used for transplantation therapy after being cultured to increase their number or formed into a desired tissue form. The culturing of cells to be used for therapy should be performed in a cell culturing clean room called "Cell Processing Center (CPC)" in accordance with Good Manufacturing Practice (GMP). The problems here are that the preparation of cells for one patient requires much effort and cost and that there is a biological contamination risk, both because cell culturing is performed manually by technical experts.

As the means for solving these problems, a system that automates cell culture processes in a closed system has been developed. By using a closed-system culture container which does not need an operation for opening/closing a lid of the culture container, the cell culture process can be automated, and the biological contamination risk can be reduced.

The major operations that are manually operated at the time of the culturing are a cell seeding operation for feeding a liquid culture medium in which cells are suspended to a culture dish and an operation for exchanging the liquid culture medium which is regularly performed during cell culturing. In the manual operation, a predetermined amount of liquid is collected by using a measuring pipette or a dispenser used by attaching a disposable dispensing tip, and the liquid is added from the liquid culture medium in the liquid bottle to the culture dish. Dispensing includes the two operations of collecting a predetermined amount of the liquid and delivering it to an objective location.

In an automated culture apparatus, there is a method for mechanizing a dispenser in the same manner and linking the manual operation, the pipetting and the movement operation in the same manner to perform the addition of a liquid as seen in Patent Literature 1, but the apparatus increases in size from the necessity for placing the entire apparatus in an aseptic environment. However, when using a pump in a dispensing operation, there is a method for connecting the space from the liquid bottle to the culture dish with a throw-away tube, and simultaneously performing feeding of a constant amount by the pump as seen in Patent Literature 2. In this case, if the inside of the tube in which the liquid is fed can be maintained in an aseptic state, the automated apparatus can be miniaturized.

CITATION LIST

Patent Literature

Patent Literature 1: Japanese Unexamined Patent Application Publication No. 2006-149268
Patent Literature 2: Japanese Unexamined Patent Application Publication No. 2007-222120

SUMMARY OF INVENTION

Technical Problem

The two aforementioned methods accompanying a dispensing operation, other than the differences in the size of the apparatuses, have differences in the frequency of the contact opportunities with the gas contacting the liquid to be dispensed. Numerous liquid culture mediums which are used in cell cultures include a base component such as $NaHCO_3$ referred to as a bicarbonate buffer system in order to control the pH of the culture medium, and accordingly, these culture media change the pH values due to contact with the air (other than 0.04% $CO_2$, 20% $O_2$ and 78% $N_2$ which are general values). Therefore, the cell culture is held inside of a $CO_2$ incubator where generally, the $CO_2$ concentration is increased to 5%, and the pH value in the culture is controlled by contacting with the gas phase which is in contact with the culture medium. Note that, air is one type of mixed gas, but in the present description, in order to distinguish both inventions, the term air indicates the gas concentration in accordance with the concentration, and the term gas indicates a gas which is intentionally adjusted and mixed other than the air.

As the first problem, there is the problem that the frequency of contact with the gas during movement in the tube of the liquid is high compared to when an instrument such as a dispensing tip or a measuring pipette was used, and the pH value of the liquid culture medium before and after feeding easily changes. Patent Literature 2 describes a method for flowing the air within an incubator into feeding tubes by a supply operation of a medicine, and suppressing the occurrence of the clogging of the feeding tube, but suppressing the qualitative changes of the liquid to be fed is not the object of the invention, and this feature is not suggested or described.

With respect to culturing techniques, normally, the operation for exchanging the liquid culture medium is performed aseptically in a safe cabinet, but the contact between the liquid culture medium and the air by the dispensing work which is performed under an atmospheric environment is unavoidable, thus, there are the problems that a skilled worker would be restricted to a constant number of processes to shorten the dispensing worktime, this kind of work know-how causes variation in the culturing techniques, and that the pH value of the liquid culture medium changes.

As the second problem, there is the problem that the pH value of the liquid culture medium stocked for the exchange changes due to temporal changes. Specifically, the processes of cell culturing are innumerable and work is performed to exchange the old culture medium with the new culture medium, thus, a large amount of liquid culture medium is prepared in a capped-bottle prior to the start of culturing, but the pH value of the prepared liquid culture medium changes over time. In the culture medium exchange work performed under an atmospheric environment, the opening and the closing of the cap of the culture medium bottle holding the liquid culture medium is performed many times. In this case, the air of an equivalent volume fraction which is reduced accompanying the use of a liquid culture medium enters the culture medium bottle, thus, the pH value of the culture medium bottle gradually increases. A skilled worker would perform a method for holding the liquid culture medium inside a $CO_2$ incubator prior to the culture medium exchange, and performing pH adjustment, but this kind of work know-how causes variation in the culturing techniques, and there are cases when the pH value of a liquid culture medium which changed greatly does not return to the pH value at the start of use by the ventilation in a $CO_2$ incubator having a 5% concentration, and these are the causes which hinder the reproducibility of the cell culture.

The object of the present invention, to solve the aforementioned problems, is to provide a liquid feeder which makes it possible to suppress the qualitative changes to a liquid culture medium to be fed to perform a cell culture, and a cell culture apparatus.

Solution to Problem

To achieve the aforementioned object, the present invention provides a liquid feeder of a configuration provided with a receptor connected to one end of a feed pipe for feeding a liquid to receive the liquid, a gas bag connected to the other end of the feed pipe, for holding a gas for suppressing qualitative changes of the liquid, and a liquid feeding mechanism part for feeding a liquid for feeding to the receptor by a feed pipe by sandwiching with a gas for suppressing the qualitative changes of the liquid, as well as a cell culture apparatus using the liquid feeder.

Further, to attain the aforementioned object, the present invention provides a liquid feeder including a holding container for holding the liquid, a receptor for receiving the liquid, a liquid feeding mechanism part which uses a feed pipe to feed the liquid in the holding container to the receptor, and a gas bag connected with the holding container for holding a gas for suppressing qualitative changes of the liquid, wherein the liquid feeding mechanism part holds a gas for suppressing qualitative changes of the liquid in a gas phase contacting the liquid in the holding container, as well as a cell culture apparatus using the liquid feeder.

Advantageous Effects of Invention

The liquid feeder according to the present invention suppresses the qualitative changes of the liquid to be fed. Further, qualitative changes of the liquid in the container after feedings are avoided.

BRIEF DESCRIPTION OF DRAWINGS

FIG. 5 is a drawing illustrating an example of a flow chart of control of the cell culture apparatus according to the third embodiment.

DESCRIPTION OF EMBODIMENTS

Below, various examples of the present invention will be explained with reference to the attached drawings. However, these examples are merely examples for actualizing the invention and they do not limit the technical scope of the invention. Further, in each drawing, similar components are identified by the same reference number.

First Embodiment

A first embodiment is a liquid feeder of a configuration provided with a receptor which is connected to one end of a feed pipe for feeding a liquid for receiving the liquid, a gas bag which is connected to the other end of the feed pipe for holding a gas for suppressing qualitative changes of the liquid, and a liquid feeding mechanism part for feeding a liquid for feeding to the receptor by a feed pipe by sandwiching with a gas for suppressing the qualitative changes of the liquid. Further, the first embodiment of the liquid feeder includes a holding container for holding the liquid, a receptor for receiving the liquid, a liquid feeding mechanism part which uses the feed pipe to feed the liquid of the holding container to the receptor, and a gas bag which is connected with the holding container for holding a gas for suppressing qualitative changes of the liquid, wherein the liquid feeding mechanism part holds the gas for suppressing qualitative changes of the liquid in the gas phase contacting the liquid of the holding container.

Below, an exemplary configuration of the liquid feeder according to the present embodiment will be sequentially described with reference to FIGS. 1 and 2.

Figure 1:
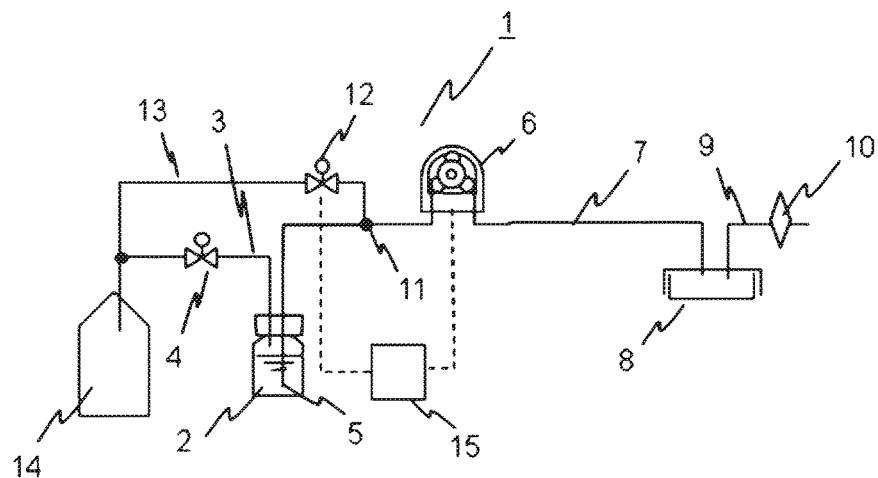
FIG. 1 is a drawing illustrating an exemplary configuration of the liquid feeder according to a first embodiment.

FIG. 1 is a drawing illustrating an exemplary configuration of the liquid feeder which utilizes the dropping of the liquid of the present embodiment. In the liquid feeder 1, 2 is a liquid bottle holding a liquid, and the liquid bottle 2 can maintain the inside in an airtight state by a lid. 3 is an air pressure adjustment pipe for air pressure adjustment provided with a lid, is connected to a gas continuity valve 4 for controlling the opening and the closing of the air pressure adjustment pipe 3, is connected via the gas continuity valve 4 to an external air introduction valve 13 which will be described later, and is connected to the gas bag 14. The valve mechanism used in the gas continuity valve 4 is preferably a solenoid valve. A so-called solenoid valve is a mechanism in which a tube is clamped to a component which is opened and closed by an electromagnet operation, and the tube is elastically deformed by turning the solenoid valve ON/OFF to open and close the pipe section. In the following description, the valve means a solenoid valve.

A supply pipe 5 is provided in the lid of the liquid bottle 2, and one end of the supply pipe 5 has an opening end on the inside of the liquid bottle 2, and the opening end is a liquid outlet port in contact with the liquid. Further, the other end of the supply pipe 5 is connected to the branch point 11 which branches the flow channels which will be explained later. 6 is a pump for constructing a part of the liquid feeding mechanism part, the pump 6 is arranged in the middle of the feed pipe 7 connected to the supply pipe 5 at the branch point 11, one end of the feed pipe 7 is connected to the branch point 11, and the other end of the feed pipe 7 is connected to the receptor 8 which receives the liquid. The receptor 8 is the culture container which is the target of the feeding. The feed pipe 7 and an air pressure adjustment pipe 9 are provided in the lid portion of the receptor 8, and the air pressure adjustment pipe 9 opens to the outside air via a filter 10 having a mesh size of 0.22 μm.

As is clear from FIG. 1, the branch point 11 which branches the flow channels is provided above the liquid level of a liquid held in the liquid bottle 2. An external air introduction valve 13 is further connected to the branch point 11 via a gas introduction valve 12. The gas introduction valve 12 opens and closes the external air introduction valve 13 which connects the branch point 11 with the gas bag 14. The amount of gas of a volume or more which is necessary for feeding the gas for suppressing qualitative changes of the liquid to be fed is held in advance in the gas bag 14. The controller 15 operates so as to better control the timing of the pump 6 and the gas introduction valve 12 and the gas continuity valve 4 which is not illustrated in the drawing.

Namely, in the configuration of FIG. 1, the feed pipe 7 branches and connects the flow channels connected to the liquid bottle 2 at the branch point 11, and the flow channels connected to the gas bag 14 via the gas introduction valve 12. The liquid feeding mechanism part for feeding the liquid to the receptor sandwiched with the gas is constituted by the pump 6 arranged in the feed pipe, the gas introduction valve 12 for introducing the gas of the gas bag to the branch point, and the controller 15 for controlling these, and furthermore, is constituted by the gas continuity valve 4 and the like for controlling the opening and the closing of the air pressure adjustment pipe 3. The branch point 11 is provided above the liquid level of a liquid held in the liquid bottle 2, and, as will be described later, when the liquid of the flow channels connected to the liquid bottle 2 is returned to the liquid bottle 2 by dropping, the flow channels are filled with the gas.

The liquid feeder 1 of the present embodiment performs a predetermined amount of feeding as described below. The flow rate of the pump 6 is set as Q (volume/time). First, if the gas continuity valve 4 is closed, and the gas introduction valve 12 is opened so that the pump 6 operates at a predetermined time (purge time), the gas within the feed pipe 7 is supplied via the branch point 11, the gas within the gas bag 14 connected to the gas passes through the feed pipe 7 to fill the pipe, and furthermore, the gas reaches the receptor 8, and the gas phase in the container which initially was air is replaced with the gas. The gas phase in the container due to the amount of gas equivalent to 100 times or more of the volume of the receptor 8 is roughly equivalent to gas concentration to be supplied. The excess gas in the container is discharged from the air pressure adjustment pipe 9 into the air via the filter 10 so that the inside of the receptor 8 is pressurized.

Next, after the gas introduction valve 12 is closed, if the gas continuity valve 4 is opened to operate the pump 6 for a predetermined time (feed time), the pump 6 supplies the gas within the supply pipe 5, and the liquid within the liquid bottle 2 connected to the gas passes through the supply pipe 5, and the feeding is started. The liquid passes through the branch point 11 and reaches the feed pipe 7. The operation time of the pump 6 is a value (feed time) obtained by dividing the total liquid amount C obtained by adding the target amount of liquid A and a volume B (hereinafter, referred to as the return amount) of the pipe corresponding to the liquid level of the liquid within the liquid bottle 2 from the branch point 11, by a flow rate Q. If the pump 6 is stopped after a predetermined time, the pipe becomes closed due to the internal structure of the pump 6, and accordingly, the liquid does not move. The gas phase of the liquid bottle 2 is supplied with the gas corresponding to the amount of liquid fed via the supply pipe 5 from the inside of the gas bag 14.

Then, if the gas introduction valve 12 is open, the gas is supplied from the gas bag 14, so that the liquid (return amount B) in the supply pipe 5 between the liquid bottle 2 from the branch point 11 position returns to the liquid bottle 2 by the potential energy generated from a dropping of the liquid. At this time, the gas connected to the liquid moving in the supply pipe 5 is the gas within the gas bag 14, and the inside of the supply pipe 5 is filled with gas from the branch point 11. The gas within the liquid bottle 2 moves to the gas bag 14 by the air pressure adjustment pipe 3 and the gas continuity valve 4 at the amount corresponding to the return amount B.

However, the liquid in the feed pipe 7 on the pump 6 side from the branch point 11 is maintained in a stop state by the internal structure of the abovementioned pump 6. Next, when the pump 6 is operated for a predetermined time (discharge time), the gas is sequentially introduced from the branch point 11, and the liquid moves in the feed pipe 7. When the front end of the liquid reaches the receptor 8, and the addition of the liquid is started, and rear end of the liquid reaches the receptor 8, and the target amount of liquid A is held in the receptor. On the other hand, the pump 6 continues to provide pressure to the gas from the branch point 12 after the liquid passed inside thereof, and continues to push the liquid from the rear end, thus, after the liquid reached the receptor 8, the gas following the liquid is supplied to the receptor 8 through the feed pipe 7. Namely, the abovementioned discharge time is the sum of the time in which the liquid is discharged from the feed pipe 7 to cause the liquid of the feed pipe 7 to empty and the time for supplying gas thereafter to supply the gas from the gas bag 14 in the receptor 8.

Figure 2:
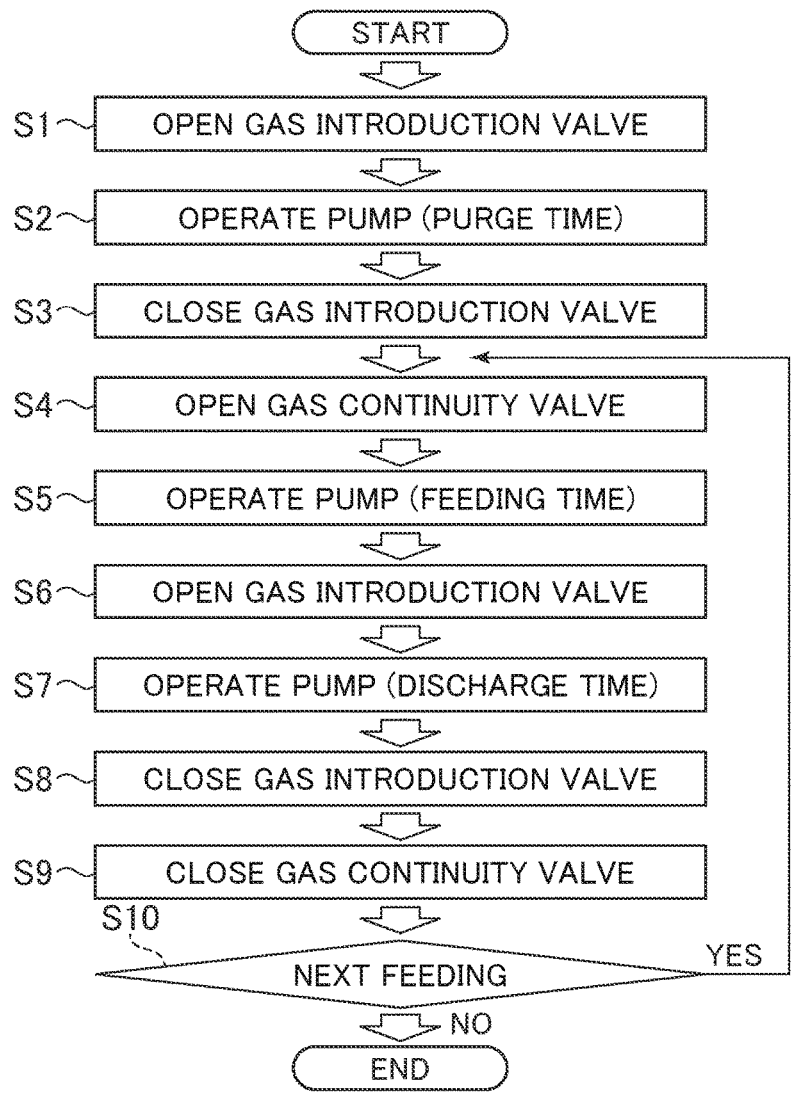
FIG. 2 is a drawing illustrating an example of a flow chart of the control of the liquid feeder according to the first embodiment.

FIG. 2 illustrates an example of a flowchart of the control with the controller 15 and the like of the liquid feeder of the present embodiment. As the initial conditions, the gas continuity valve 4 and the gas introduction valve 12 are closed, and the pump 6 is stopped. Regarding "START", the gas introduction valve 12 is opened (S1), operated by providing a purge time to the pump 6, the gas for suppressing the qualitative changes of the liquid is injected, and the feed pipe 7 and the inside of the receptor 8 is replaced with the gas (S2). The gas introduction valve 12 is closed (S3), the gas continuity valve 4 is opened (S4), and then, operated to provide a feed time to the pump 6, and the feeding is performed (S5). Next, the gas introduction valve 12 is opened (S6), and then, operated to provide a discharge time to the pump 6 (S7). After an arbitrary time, the gas introduction valve 12 is closed (S8), and the gas continuity valve 4 is closed (S9). It is verified as to whether there is a subsequent feeding operation (S10), and when a subsequent feeding is performed, the initial return operation is repeated, and when there is no subsequent feeding operation, the operation is completed (END).

If the liquid feeder 1 of the present embodiment is used, the qualitative changes of the liquid to be fed are suppressed. As the reason therefor, if the gas for suppressing the qualitative changes of the liquid to be fed is held in the gas bag 14, and the liquid feeding mechanism part is operated, in other words, if the gas introduction valve 12 opens to operate the pump 6, the feed pipe 7 and the receptor 8 are filled with the suppressing gas prior to feeding. Then, if the liquid feeding mechanism part is operated, i.e., the gas introduction valve 12 is closed to operate the pump 6, the liquid moves from the liquid bottle 2, and after the movement of a predetermined amount from the liquid bottle 2, if the gas introduction valve 12 is again opened, the liquid is fed by sandwiching both of the front end and the rear end with the gas for suppressing the qualitative changes of the liquid.

Additionally, the reason that qualitative changes of the liquid within the receptor 8 immediately after feeding are avoided in the liquid feeder of the present embodiment is that the pump 6 operates to make the entire amount of the liquid reach the receptor 8 by the liquid being in a state in which the front end and the rear end are sandwiched with the gas. At this time, the pump 6 continues to provide pressure to the gas for suppressing qualitative changes of the liquid after the liquid has passed through, and continues to push the liquid from the rear end, thus, after reaching the liquid, the suppressing gas following the liquid continues to be supplied to the receptor 8, thus, the receptor 8 is filled with the liquid and the suppressing gas immediately after feeding and accordingly, the liquid does not contact the air.

Additionally, qualitative changes to the liquid over time are suppressed in a state stored in the liquid bottle 2. As the reason therefor, the gas phase which connects to the liquid in the liquid bottle 2 due to the feeding operation is stored in the liquid bottle 2 in a state in which the liquid surface is sandwiched by the suppressing gas in the front end, and the contact with the air by the liquid is reduced.

Furthermore, when there is a subsequent feeding operation, the gas concentration of the supply pipe 5 increases after the initial operation, thus, is advantageous in the suppression of qualitative changes of the liquid. By using this, the initial feeding is not performed, and an application which uses the liquid obtained by the second feeding operation is possible.

When the above-stated liquid feeder of the present embodiment is used in the liquid culture medium in which the cells in the cell culture were suspended or the feeding of the liquid culture medium alone, the effect thereby is remarkable. The ph value of the liquid culture medium changes due to contact with the air, but in the device configuration of the present embodiment, if a gas having a $CO_2$ concentration suitable for maintaining the pH value is held in the gas bag 14 and the liquid culture medium is fed from the liquid bottle 2 by the operation flow shown in FIG. 2, the liquid culture medium is fed by sandwiching the front end and the rear end by a gas having a suitable $CO_2$ concentration, thus, the change of the pH value of the liquid culture medium during feeding can be controlled.

Note that, as stated above, a roller pump is suitable for the pump 6 of the liquid feeding mechanism part. However, pumps of other types such as a diaphragm pump and a gear pump can be used. The roller pump which is a so-called squeezing pump and the tube pump are mechanisms for feeding the gas and liquid in the tube by winding the tube around the roller attached to a motor rotating shaft and elastically deforming the tube by a motor rotation. In the cell culture apparatus, it is necessary to assure the sterilization properties of the tube for feeding the liquid, and the roller pump in which the tube can be exchanged at the time of the usage is useful. Certainly, any supply pump can be used when the sterilization can be performed to the inside of the pump prior to use.

Further, it is necessary to have a structure in which the liquid in the pump does not move at the time of stopping the pump. However, at the time of using the pump of the configuration in which the liquid moves, the pump can be applied to the apparatus of the present application if the pipeline is configured with a check valve which limits the flow to the side of the feeding bottle, provided in the front or rear of the pump. Specifically, the filter 10 connected to the receptor 8 omits the valve in order to simplify the explanation, but the valve for opening and closing the air pressure adjustment pipe 9 and the receptor 8 after feeding provided with a check valve can be kept airtight, and can be utilized as a culture container when seeding cells.

In the liquid feeder of the present embodiment, when feeding the same amount of liquid to a plurality of containers, the branch points corresponding to the number of containers (not shown) and a container opening/closing valve corresponding to each of the branch points are provided between the pump 6 and the receptor 8, only the container opening/closing valve connected to the receptor 8 to be fed is opened, and the aforementioned operation can be repeated, so that the same amount of liquid can be fed. Further, the discharge pipe 7 is ventilated by the gas during the feeding so that the liquid culture medium is not maintained in the pipeline, thus, there is no risk of clogging even in a feeding operation conducted in a dry environment.

Further, the tubes used in the air pressure adjustment pipe 3, the feed pipe 7 and the external air introduction valve 13 in the liquid feeder of the present embodiment are preferably a flexible resin material, and, a material in which the gas permeability is low is good from the necessity that the gas passes through the inside, and ethylene vinyl alcohol (EVOH), polyester, polyvinyl chloride, and the like can be used. It is necessary to use a high elasticity rubber to close the tube with a solenoid valve, but a rubber material having low gas permeability is expensive and there are few varieties, thus, the length of the rubber material used should be minimized.

Specifically, a bag-shape having a connection part with the external air introduction valve 13 is more preferable as the shape of the gas bag 14 in the liquid feeder of the present embodiment. A bag having a bottle shape can be used as the bag for holding the gas, but if a predetermined gas is to be held at the desired gas concentration, gas concentration management which requires a process for exchanging from the air to the gas is not easy, and furthermore, the point that when an excess amount is held, the pressure is held on the inside must be considered. If the gas bag is a bag-shape, when filling the gas, the gas on the inside is discharged by crushing the bag in advance, then, when filling with the desired gas, it is easy to hold the gas within the volume thereof at the desired gas concentration. Further, when holding an excess amount, if the filling regions are separated, the point that the excess gas is discharged to hold the inside at an atmospheric pressure equivalent is useful. A resin material is preferable as the material of the gas bag, and furthermore, a material in which the gas permeability is low is good from the necessity of holding the gas on the inside, and ethylene vinyl alcohol, polyester, polyvinyl chloride and the like can be used.

As explained above, the liquid feeder according to the first embodiment suppresses the qualitative changes of the liquid to be fed, and specifically, qualitative changes of the liquid within the container immediately after feeding are avoided.

Second Embodiment

Next, an exemplary configuration of the liquid feeder according to a second embodiment will be explained with reference to FIG. 3. The liquid feeder 16 of the second embodiment is an example of the liquid feeder which uses a liquid bag in place of the liquid bottle of the first embodiment. Namely, a liquid feeding mechanism part provided with a liquid bag 17 for holding the liquid, flow channels connecting the feed pipe 7 to the liquid bag 17, and a branch point 11 branching and connecting to the flow channels connected to the gas bag 14, includes a pump 6 arranged in a feed pipe 7 and a gas introduction valve for introducing the gas from the gas bag 14 to the branch point 11, wherein when the branch point 11 is provided above the liquid level of a liquid held in the liquid bag 17 and the liquid of the flow channels connected to the liquid bag 17 returns to the liquid bag 17 due to the dropping, the flow channels are filled with the gas.

Figure 3:
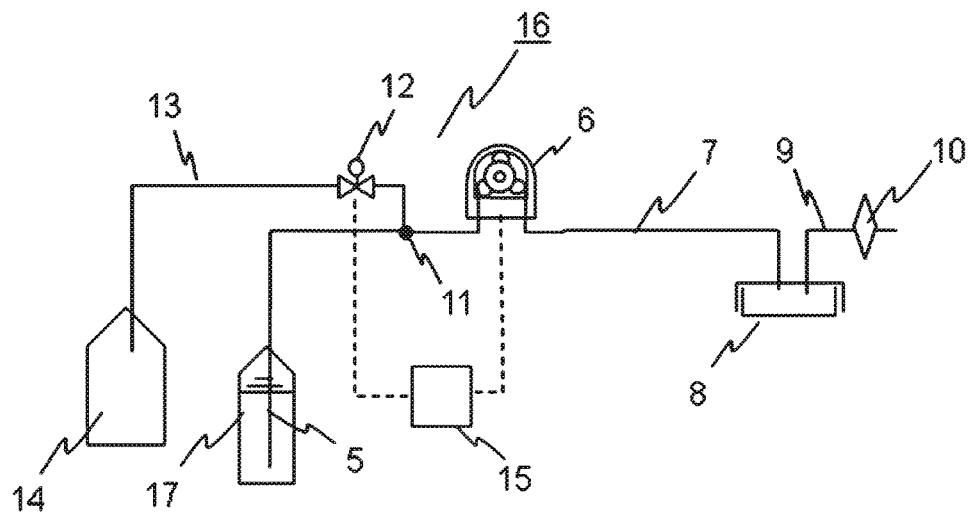
FIG. 3 is a drawing illustrating an exemplary configuration of the liquid feeder according to a second embodiment.

The liquid bag 17 is used in the liquid feeder of the present embodiment in the same manner shown in FIG. 3, thus, as in the first embodiment, the air pressure adjustment pipe 3 and the gas continuity valve 4 are not used. The liquid bag 17 is used in the liquid holding part, but from the supply pipe 5 to the controller 15, the configuration is the same as the configuration of the first embodiment, thus, an explanation of the common mechanisms and operations is omitted.

When using the liquid bottle 2 of the first embodiment, a solid shape such as a bottle with a lid is easy to insert with a liquid, and the confirmation of the amount of liquid is also easy and convenient, whereas there is the following effect when the bag-shaped liquid bag 17 of the present embodiment is used.

The liquid bag 17 is a bag-shape having a supply pipe 5, and has a sealed structure, thus, when filling the liquid, after discharging the gas on the inside which is crushed in advance and filling the desired liquid, the mixture of the air on the inside is restricted so that only the desired liquid can be held in the volume thereof. However, at the time of feeding, if a branch point 11 is provided above the height in the liquid held in the liquid bag 17 in the same manner as the first embodiment, the returned liquid by the dropping of the liquid is performed in the same manner as in the first embodiment, and the air pressure adjustment corresponding to the increase or the decrease of the quantity of the liquid in the liquid bag 17 is adjusted by deforming the liquid bag 17.

Therefore, the configuration of the liquid feeder of the present embodiment, compared to the liquid feeder which used a liquid bottle, restricts the mixture of the air on the inside and can minimize the frequency of contact of the air and the liquid, and thus, has the effects that the liquid is not connected to the air and that qualitative changes of the liquid over time can be further avoided.

Third Embodiment

The present embodiment is an example of the cell culture apparatus which used the liquid feeder described in the first embodiment. Below, an example of the cell culture apparatus provided with feeding control mechanism for performing the supply or discharge of the liquid culture medium to the cell culture container which is a receptor will be explained using FIG. 4 and FIG. 5.

Figure 4:
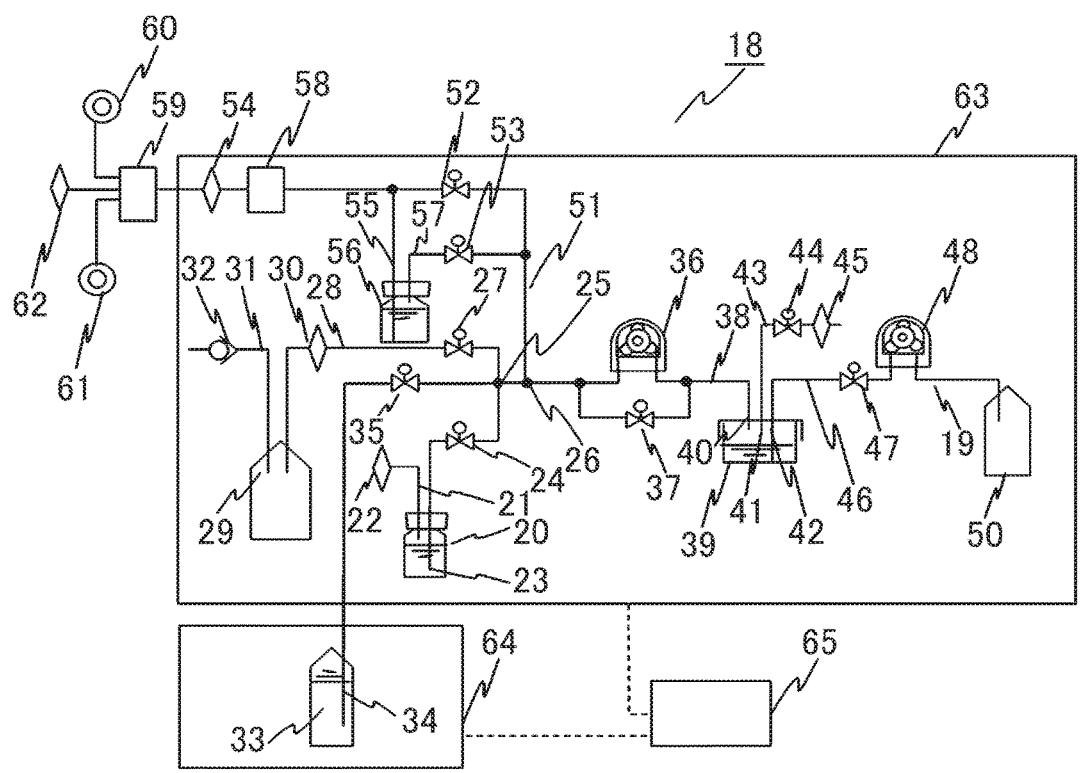
FIG. 4 is a drawing illustrating an exemplary configuration of the cell culture apparatus according to a third embodiment.

FIG. 4 is a drawing showing an exemplary configuration of the cell culture apparatus which used the liquid feeder described in the first embodiment. In FIG. 4, a thermostatic chamber 63 of the cell culture apparatus 18 maintains the cell culture at the optimum culturing temperature by the control of the controller 65, and holds the culture container 39 on the inside thereof. The liquid feeder and the culture container explained in the first embodiment arranged in thermostatic chamber 63 and the refrigerator 64 can be exchanged as integrated flow channels, the integrated flow channels are removed in the culture work to be used in arranging the new flow channels.

The configuration for feeding the liquid or the gas to the culture container 39 of the cell culture apparatus of the present embodiment will be explained. The inside of the cell bag 20 maintaining the cell suspension having suspended cells can be maintained airtight. One end of the supply pipe 23 has opening ends on the inside of the cell bag 20 and is a liquid outlet port in contact with the held cell suspension. The supply pipe 23 is connected to the branch point 25 which branches the flow channels corresponding to the branch point 11 of FIG. 1 via an opening/closing valve 24.

The branch point 25 is a plurality of junctions, one of which is connected to a gas introduction valve 27 for controlling the external air introduction valve 28, and one of which is connected to a supply valve 35 for controlling the supply pipe 34 which supplies the liquid, and furthermore, is connected downstream to a gas supply pipe 51 from a ventilation branch point 26 which will be described later. Namely, the junction is provided with the flow channels which connect a feed pipe 38 to the liquid bottle 20 and the branch point 25 for branching and connecting to the flow channels which are connected to a gas bag 29, the liquid feeding mechanism part includes a pump 36 arranged in the feed pipe, and a gas introduction valve 35 for introducing the gas from the gas bag 29 to the branch point 25, and the branch point 25 is provided above the liquid level of the liquid held in the liquid bottle 20, and when the liquid of the flow channels which are connected to the liquid bottle 20 returns to the liquid bottle 20 by dropping, the flow channels are filled with the gas for suppressing qualitative changes of the liquid.

Specifically, the supply pipe 34 leading to the supply valve 35 is connected to the culture medium bottle 33. The culture medium bottle 33 corresponds to the liquid bottle 2 of the first embodiment, is a liquid bottle for holding the liquid culture medium for the culture medium exchange, and holds the liquid culture medium in a refrigerator 64 at a low temperature. The cell bag 20 is provided with an air pressure adjustment pipe 21 for air pressure adjustment in the cap part thereof, and the filter, or the gas continuity valve 22 are connected to the air pressure adjustment pipe 21. The illustration is omitted for simplification, but when using the gas continuity valve 22 which can control the opening and closing of the air pressure adjustment pipe 21, the gas continuity valve 22 is connected to the external air introduction valve 31 which will be described later and the gas bag 29 via the gas continuity valve 22 in the same manner as the gas continuity valve 4 of FIG. 1.

The external air introduction valve 28 leading to the gas introduction valve 27 is connected to the gas bag 29 via the filter 30, and the gas for suppressing the changing of the pH value of the cell suspension or the liquid culture medium can be held at the optimum concentration in the gas bag 29 corresponding to the gas bag 14 of the first embodiment. The gasbag 29 of the present embodiment is provided with a check valve 32 via the air pressure adjustment pipe 31, and the opening end of the check valve 32 opens to the air within the thermostatic chamber 63. The check valve 32 which is also referred to as the check valve restricts the direction in which the fluid can flow on the inside to one direction, thus, the present embodiment flows the gas from the air pressure adjustment pipe 31 in the direction of the space of the thermostatic chamber 63. The branch point 25 is provided above the liquid level of the liquid held in the cell bag 20 in the same manner as the branch point 11 of the first embodiment, and is provided above the liquid level of a liquid held in the culture medium bottle 33.

The ventilation branch point 26 is connected to the supply pump 36. Further, a third gas opening/closing valve 37 is provided and is connected to the feed pipe 38 in order to bypass the supply pump 36. The culture container 39 is connected to the feed pipe 38. The flow channels downstream from the ventilation branch point 26 may collectively refer to all of the feed pipes.

In the appearance, the culture container 39 is a hermetical container including a main body and the cap part, and inside, the container can hold and culture cells in the inner bottom portion of the main body. Three ports are provided in the cap part, and are respectively composed of the feeding port 40, the air pressure adjustment port 41 and the discharge port 42. The feeding port 40 is connected to the feed pipe 38, and the opening ends are provided in the vicinity of the inside of the cap part. The air pressure adjustment port 41 and the opening ends thereof are provided in the vicinity of the inside of the cap part, and are connected to the air pressure adjustment pipe 43. The air pressure adjustment pipe 43 is controlled by the air pressure adjustment valve 44, and furthermore, the air in thermostatic chamber 63 is opened via the filter 45. The discharge port 42 is connected to the discharge pipe 46, and the opening ends are provided in contact with the vicinity of the inner bottom surface.

If the air pressure adjustment valve 44 is open and the supply pump 36 operates, and only the opening/closing valve 24 is opened, the cell suspension of the cell bag 20 is fed to the culture container 39, if only the culture medium opening/closing valve 35 and the gas continuity valve 22 are opened, the liquid culture medium of the culture medium bottle 33 is fed to the culture container 39, and if only the gas introduction valve 27 is opened, the gas of the gas bag 29 is supplied to the culture container 39. At this time, in any of these cases, the original gases which were in the culture container 39 are released to the air in thermostatic chamber 63 via the filter 45 due to the pressure of the supply pump 36, and the inside of the culture container 39 is held at a normal pressure.

Next, the configuration for discharging the liquid or the gas maintained within the container by the culture container 39 will be explained. The discharge pipe 46 connected to the culture container 39 is connected to the discharge pump 48 via the discharge control valve 47, and the drain pipe 49 and the drain bag 50 are air-tightly connected to the discharge pump 48. When the gas introduction valve 27 and the third gas opening/closing valve 37 are opened and the discharge pump 48 operates, if the discharge control valve 47 is opened, the liquid held in the bottom portion of the culture container 39 is fed to the drain bag 49. At this time, the liquid and the gas corresponding to the amount of discharge from the discharge pump 48 from the inside of the culture container 39 decreases, and the gas from the gas bag 29 flows into the culture container 39 due to the pressure of the discharge pump 48, thus, the inside of the culture container 39 is held at a normal pressure.

The configuration for ventilating the gas phase of the culture container 39 with the gas is explained below. 59 is a gas mixer, and is connected to a reduced pressure 100% $CO_2$ cylinder 60, a nitrogen cylinder 61, and a filter 62 upstream, so that clean air can be supplied via the filter 62 from the filter 62 which is open to the air. It is possible for the gas mixer 59 to generate an arbitrary gas concentration, and as an example, when 5% $CO_2$ with respect to the air is required, the $CO_2$ gas supplied from the 100% $CO_2$ cylinder 60 is diluted with the air supplied from the filter 62 so that the target gas concentration can be produced, and when a 5% $CO_2$ and 1% $O_2$ gas is required as the low oxygen gas, the $CO_2$ gas supplied from the 100% $CO_2$ cylinder 60 is diluted with the nitrogen cylinder 61 so that the target gas concentration can be produced.

A flow rate regulator 58 is connected to a gas mixer 59 via a filter 54, and can control the flow rate of the gas adjusted to the target gas concentration by the gas mixer 59 from 0 to an arbitrary amount. The outflow side of the flow rate regulator 58 is branched, and is connected to a first gas opening/closing valve 52 and a humidifying tube 55 for controlling the ventilation pipe 51. The humidifying tube 55 is connected to a humidifying bottle 56 holding the sterile water therein, and is connected to a second gas opening/closing valve 53 for controlling a humidifying tube 57 provided in a humidifying bottle 56. The first gas opening/closing valve 52 and the second gas opening/closing valve 53 are joined, and pass through the ventilation pipe 51 to connect to the ventilation branch point 26.

The liquid culture medium in the cell culture suppresses the pH value from changing over time, thus, it is necessary to periodically perform gas exchange from the surface of the liquid culture medium with the $CO_2$ gas. Additionally, it is necessary to suppress the thickening of the liquid culture medium component due to the evaporation of the liquid culture medium. When the gas phase of the culture container 39 undergoes gas exchange and heating, after the second gas opening/closing valve 53, the third gas opening/closing valve 37 and the air pressure adjustment valve 44 are opened, the gas adjusted by the gas mixer 59 is controlled to the optimum flow rate by the flow rate adjustment of the flow rate regulator 58, and the sterile water in the humidifying bottle 56 is humidified while passing through via the humidifying tube 55. The $CO_2$ gas which became foamy in the humidifying bottle 56 remains in the gas phase in the humidifying bottle 56, passes through the ventilation pipe 51 and the third gas opening/closing valve from the humidifying tube 57, and reaches the culture container 39.

When filling the required amount of a predetermined gas component in the gas bag 29, after the first gas opening/closing valve 52 and the gas introduction valve 27 are opened, the gas adjusted by the gas mixer 59 due to the flow rate adjustment of the flow rate regulator 58 passes through the ventilation pipe 51 and the external air introduction valve 28 and reaches the gas bag 29. The volume of the gasbag 29 is desirably a volume greater than the amount of gas required for cell culturing one time, but when the required amount of liters (L) is produced, the apparatus in which a space volume suitable for the required amount is maintained inside the apparatus increases in size. Therefore, only the minimum necessary amount is held prior to the culture medium exchange, and the gas bag can become smaller than by periodically filling and using during the culture period.

At this time, filling an excessive amount of gas during the filling causes the pressure maintained in the gas bag 29 to be higher than the normal pressure, so that an external force other than the discharge pressure of the pump is provided to the liquid to be fed in the gas introduction during feeding. Further, a method for calculating the residual amount after the previous use to determine the replenishing amount, and the method for using an internal pressure sensor of the gas bag to manage the amount of gas supplied make the control complicated. The present embodiment provides a check valve 32 via the air pressure adjustment pipe 31 when an excessive amount of gas is filled, thus, the excess gas is discharged in the air in the thermostatic chamber 63 by the check valve 32, and when the internal pressure of the gas bag 29 is in the range of the atmospheric pressure, the discharge of the gas is stopped. In short, when replenishing, regardless of residual amount from the previous use of the gas bag, it is possible to hold a fixed amount of gas.

Next, the operation of the cell culture of the cell culture apparatus in the present embodiment will be explained. FIG. 5 shows a flowchart of the entire operation of the cell culture in the cell culture apparatus controlled by the controller 65. Regarding "START", after the flow channels were placed in thermostatic chamber (S01), the cell bag holding a separately prepared cell suspension and the culture medium bottle 20 holding the liquid culture medium are connected to the flow channels (S02). Next, the gas is automatically filled in the gas bag (S03). After the gas is supplied to the culture container, the cell suspension is fed (S04). The humidified gas is supplied directly to the culture container, and the cells are kept at a constant temperature and left standing (S05). Whether the exchange of the liquid culture medium should be started is determined by the state of the progression of the cell culture (S06). In exchanging the liquid culture medium, after filling the gas in the gas bag (S07), and after the old culture medium of the culture container is discharged (S08), the new liquid culture medium is fed from the culture medium bottle (S09). Subsequently, the humidified gas is supplied and left standing (S10), is continuously determined by the state of the progression of the cell culture (S11), and the culture medium exchange is performed again. When the cell culture is completed, the automatic culturing is ended, and the extraction of the cultured cells is performed manually (S12), the drain bag is recovered for confirmation by the presence or absence of bacterial growth (S13), and the used flow channels were removed from thermostatic chamber to complete the operation (END).

A specific example of a method of preparing a corneal epithelial tissue by a corneal epithelial cell culture using the cell culture apparatus and the liquid feeder of the Third example, and the results thereof will be described below.

<Cell Culture Apparatus and Constitution of Liquid Feeder>

A thermostatic culture apparatus (Toyo Engineering Works, Ltd., model number: TVHA60WA12A) was used in thermostatic chamber, and thermostatic culture apparatus was operated while setting an inner temperature of 37° C., an electronic cooling/heating Low thermostatic device (Toyo Engineering Works, Ltd., model number: THS030PA) was used as the refrigeration unit, and the refrigeration unit was operated while setting the inner temperature to 4° C.

A pinch valve (fluid pressure 0.15 MPa, Takasago Electric, Inc. model number: PSK-1615NC-9) was used as the solenoid valve. A silicone rubber tube (inner diameter 1/16 inch, outer diameter 1/8 inch, Saint Gobain K.K. model number: 3350) was used as the supply pipe corresponding to the solenoid valve. A tube pump (discharge/intake pressure +/−0.1 MPa, Welco Co. Ltd., model number: DSW2-S1AA-WP) was used as each pump and a silicone rubber tube (inner diameter 1/16 inch, outer diameter 1/8 inch, Saint Gobain K.K. model number: 3355L) was used as a squeezing tube. Since a roller of this product is removable from a motor of a body, a sterilization operation can be performed in a state where the silicon rubber tube (13 cm length) is wound around the roller. The flow rate of the pump was 0.15 mL/second based on the actual measurement in the case of DC 12 V input.

A FLEXBOY bag (EVA, EVOH Double structure, volume 150 mL, Sartorius AG, model number: #FFB102643) was used for the cell bag.

A Closed-system three-neck flask (volume 500 mL, Corning Incorporated model number: #11440) was used for the culture medium bottle. The product includes a container, a cap part, and a lid part which have been previously sterilized, a pipeline which is provided in the cap part for adjusting the air pressure, and a filter having a mesh size of 0.22 μm.

A Flexboybag (EVA, EVOH Double structure, volume 0.5 L, Sartorius AG, model number: #FFB102670) was used for the drain bag.

A Flexboybag (EVA, EVOH Double structure, volume 1 L, Sartoris AG model number: #FFB103547) was used for the gas bag, and a check valve (ARAM Corporation model number: #PRC15, cracking pressure 0.2 to 1.5 kPa) was used for the check valve connected to the one Luer port part.

A gas washing bottle (volume 500 mL, AS ONE Corporation model number: 6-129-02) and a Kerami filter (filter size 15×15 mm, AS ONE Corporation model number: 2-554-10) were used in combination for the humidifying bottle and for the gas exchange unit respectively.

A Midisarts 2000 (mesh size 0.22 μm, Sartoris AG, model number: #17805-E) was used for the filter for contacting with the outside air of the gas introduction valve or the humidifying bottle.

Tygon ND-100 (inner diameter 1/16 inch, outer diameter 1/8 inch, Saint Gobain K.K., model number: #ADF00002) which is vinyl chloride was used as the material for the tubes other than the closed region of the solenoid valve and the squeezing region of the pump part. An SMC coupling (Colder Products Company) series was used as the branches and the joints of the tube. In detail, a Y Fitting (diameter of joint: 1/16 inch, model number: #HY291) was used as a two-branch joint, and a Straight Fitting (diameter of joint: 1/16 inch, model number: #HS291) was used as a straight line joint.

The culture container 39 shown in FIG. 4 was made by injection molding using polycarbonate as the material. A 35 mm surface-treated cell culture dish, Corning Incorporated model number: 430165, was used as the container surface which holds the cells.

<Method of Manufacturing Closed System Flow Channels>

The abovementioned components were assembled aseptically in a safe cabinet to manufacture the flow channels. After the flow channels were put in a sterilization bag and sealed, and a 15 kGry radiation sterilization process was performed at the request of a gamma ray sterilization process operator.

<Preparation of Corneal Epithelial Cells>

The flow of the culturing method of the corneal epithelial cells of the present example will be explained. As the corneal epithelial cells, the corneal epithelial cells collected in a conventional manner from the corneal limbus of a rabbit eyeball purchased from Funakoshi Corporation were suspended in a culture medium to give a concentration of $4\times10^4/cm^2$, and maintained in a cell bag 20. The culture medium used a 5% FBS-containing KCM culture medium. As the culture medium for exchange, 500 mL of KCM culture medium was maintained in the same culture medium bottle 33, and arranged in a refrigerator 64.

<Start of Culture of Corneal Epithelial Cell>

After arranging the sterilized flow channels in the apparatus of the present embodiment shown in FIG. 4, and connecting each of the solenoid valves with the cell culture container 39 by the rubber tube, the configuration was maintained in a thermostatic chamber at a constant temperature of 37° C. After the cell bag prepared as stated above and the culture medium bottle were connected to the flow channels, the automatic culturing operation was started. The feed amount of the cell suspension was 1.5 mL, and the feed amount of the culture medium exchange was also 1.5 mL. At the time of discharging, the discharge amount from the upper layer was set at 3 mL and the discharge from the lower layer was set at 3 mL in order to discharge the liquid completely. The gases maintained in the gas bag and the gas concentrations of the gases supplied were set to 5% $CO_2$, 20% $O_2$ and 78% $N_2$, the humidified gas supplied was controlled to a humidity of 95% H, the gas was delivered at a gas delivery flow rate of 0.1 L/min, and the gas supply time was set at 2 minutes (200 mL) for injecting the gas in an amount exceeding the internal volume of the 20 $cm^3$ culture container. The aforementioned operation flowchart was based on the outline of FIG. 5.

The exchanging of the culture medium was performed once on Day 5, Day 7, Day 9, Day 10, Day 11, Day 12, Day 13, Day 14, Day 15, and Day 16 after the day on which culturing began. The feeding of the humidified gas was performed 42 times per day, every 20 minutes. While not shown, microscopic observations of the state of the cells were performed once a day starting from Day 5, and ten areas were obtained from the culture cell surface of the culture container, and were used as the data for determining the cell growth state.

<Method of Recovery of Corneal Epithelial Tissue>

After the culture medium exchange operation on Day 16, the cell culture was completed and the cell culturing containers were removed as described above. The cell culturing containers were placed in a safety cabinet and allowed to stand at room, temperature (about 25° C.) for 30 minutes. The cell insert container was removed, and then, the cells contained therein were subjected to a trypsin treatment in accordance with a predetermined method and the cells were separated and recovered from the surface of the culture.

<Control Test Method>

As the culture dish, a 35 mm cell culture surface treated dish, Corning Incorporated model number: 430165 was used. The temperature environment and the $CO_2$ gas environment were set to a temperature of 37° C., a humidity of 95% H, and a 5% $CO_2$ concentration, a $CO_2$ incubator, Sanyo Electric Co. Ltd., model number: MCO19-AIC, and cell culturing was performed. As the control cells, cells similar to those used above were used.

Cell seeding and culture medium exchange were manually performed and the liquid amount added using a sterilized dispenser (PIPETMAN, GILSON Inc., model number: P5000) was equal to that described above. The frequency and interval of culture medium exchange were the same as in the above embodiment and the control of the $CO_2$ gas was performed under the same conditions throughout culturing. Note that, the culture medium exchange was performed by placing the culture dish on a 37° C. hotplate to maintain the temperature.

<Culture Test Results>

The corneal epithelial cells prepared using the cell culture apparatus of the present embodiment were sheet-like cells having a constant thickness, and a stable separation and recovery was possible. Also in comparison of microscopic images during growth, there were no abnormalities in the growth of the cells. However, cultured cells obtained by the control test and collected were equivalent in shape. The number of cells after proliferation proliferated to approximately 50 times (conversion amount) the cells seeded, and were slightly better compared to the control test results.

Cultured cells were observed by preparing sections of the corneal epithelial tissue and subjecting the sections to hematoxylin-eosin staining and immunohistostaining, and as a result, it was found that a CK protein family which was expressed in epithelial cells was expressed in all the cells in the present example group and the control test group. The CK3 which is expressed in differentiated corneal epithelial cells were expressed in cells other than the basal layer, and Claudin 1 which is a closed binding protein necessary for the barrier function of the epithelial tissue, was expressed in the outermost layer, and there were no significant differences between two groups.

The qualitative changes of a liquid culture medium to be fed, specifically, the pH value which is the first problem according to cell culture apparatus described in detail in the present embodiment is suppressed. As the reason therefor, if the gas including a preferable predetermined concentration of $CO_2$ is maintained in the gas bag 29 in order to control the qualitative changes of a liquid culture medium to be fed, specifically, the pH value, and the gas introduction valve 27 is opened so as to use the supply pump 36, the feed pipe 38 and the culture container 39 can be filled with the gas in advance of the feeding. Then, if the gas introduction valve 27 is closed, the opening/closing valve 24 opened, and the supply pump 36 is used, after the cell suspension moves from the cell bag 20, and a predetermined amount moves from the cell bag 20, if the gas introduction valve 27 is opened, the cell suspension can be fed by sandwiching the front end and the rear end with the gas. When feeding the liquid culture medium, if the supply valve 35 is opened and the supply pump 36 is used in the same manner, the liquid culture medium moves from the culture medium bottle 33, and after a predetermined amount moves from the culture medium bottle 33, if the gas introduction valve 27 is opened, the liquid culture medium can be fed by sandwiching the front end and the rear end with the gas.

Additionally, the qualitative changing of the cell suspension or the liquid culture medium in the container immediately after feeding, specifically, the pH value, is avoided. As the reason therefor, the supply pump 36 is used so that the entire amount of the liquid reaches the container 39 in a state in which the liquid sandwiches the front end and the rear end with the gas. At this time, the supply pump 36 continues to provide pressure to the gas after the passing through of the cell suspension or the liquid culture medium, and continues to push the cell suspension or the liquid culture medium from the rearward direction. After the cell suspension or the liquid culture medium reaches the culture container 39, the gas continuing to the cell suspension or the liquid culture medium continues to be supplied to the container 39, thus, the culture container 39 immediately after feeding is filled with the cell suspension or the liquid culture medium and the gas, and accordingly, the cell suspension or the liquid culture medium does not contact the air.

Furthermore, the temporally qualitative changing of the liquid in a stored state which is the second problem, specifically, the pH value, is suppressed. As the reason therefor, the gas phase contacting with the liquid culture medium within the culture medium bottle 33 due to the feeding operation is stored in a state in which the front end contacts the gas, and the container restricted the mixing of the air, thus, regarding the liquid culture medium, the contact with the air is reduced.

Furthermore, when there is a subsequent feeding operation, the gas concentration within the supply pipe 23 or 34 increases after the initial operation, thus, this is advantageous for controlling the qualitative changing of the cell suspension or the liquid culture medium, specifically, the pH value. By using this, the initial feeding is not performed, and an application which uses the cell suspension or the liquid culture medium obtained by the second feeding operation is possible.

Furthermore, the liquid feeder and the cell culture apparatus described in the present embodiment have the following effect. In the present embodiment, a general dry incubator can be used for thermostatic chamber for maintaining the culture container at a constant temperature. The $CO_2$ incubator used in culturing techniques, other than maintaining a constant temperature, has a humidity maintenance function and a $CO_2$ concentration maintenance function, is generally manufactured to be highly airtight, and has a high cost due to the necessity of a plurality of control circuits. Further, an evaporation tray is provided in the culture area to manage the water level of the sterile water in order to maintain the humidity, and at times, maintenance such as replenishing is necessary. The automated culture apparatus described in Patent Literature 2 is an example of a cell culture apparatus incorporated with a mechanical device on the inside of a $CO_2$ incubator, but the present embodiment in which a dry incubator maintained at a constant temperature, has a gas bag and supplies a gas during feeding has the following three advantageous points.

The first is that the gas is not obtained from the space of a large capacity $CO_2$ incubator, only the amount which is necessary for directly feeding from the $CO_2$ cylinder which is the source of the gas supplied is held, thus, a predetermined gas concentration can be easily prepared. Therefore, the flow channels are installed at the start of culturing, thus, there is the advantageous point that the feeding can be started at a time in which the relaxation time until the start of culturing is short.

The second is that the gas is a gas which maintains the pH value in the culture supplied directly from the $CO_2$ cylinder and the like which is the source of the gas supplied in the same manner, thus, by responding to a changing of the pH value in the culture, the gas concentration of the gas to be supplied can be changed immediately. Further, a gas suitable for maintaining the pH value of the liquid culture medium is held in the gas bag in advance, thus, even if a situation such as a $CO_2$ cylinder residual amount shortage occurs, this gas can be substituted as the source of the gas supply.

Additionally, as an unexpected situation in automatic culturing, even if there is the possibility that the door of thermostatic chamber is opened to inspect the inside, the gas for maintaining the pH value of the culture medium is not obtained from the space of a large capacity $CO_2$ incubator, and is supplied from a small closed space, and thus, is a method which is hardly influenced by environmental changes during automatic culturing.

As stated above, the liquid feeder and the cell culture apparatus according to the present invention control the qualitative change of the liquid to be fed. Further, the qualitative change of the liquid in the container immediately after feeding is avoided. As the reason therefor, the gas for suppressing the qualitative change of the liquid to be fed is held in the gas bag, and the gas can be filled in the feed pipe and the target container in advance of feeding. Then, by supplying the gas from the gas bag at a time when the feeding started, the liquid moved from the liquid holding container, and a predetermined amount of liquid moved from the liquid holding container, the liquid is fed by sandwiching the front end and the rear end with the gas.

Additionally, by the liquid being in a state in which the front end and the rear end are sandwiched with the gas, the feeding continues so that the entire amount of the liquid reaches the target container. Then, if the gas continues to be supplied, and the liquid is pressurized from the rear end, the gas continuing to the liquid continues to be supplied to the target container after the liquid reached the target container, thus, the inside of the container is filled with the liquid and the gas immediately after feeding, and accordingly, the liquid does not contact with the air, and qualitative changes of the liquid can be avoided.

Furthermore, the gas bag is connected with the liquid holding container so as to continue to block the air, and the gas reduction equivalent of the liquid is filled and maintained in the gas phase of the liquid holding container, thus, the liquid is not in contact with the air.

Note that, the present invention is not limited to the aforementioned examples, and various modification examples can be included. For example, the embodiments have been described in detail to clearly understand the present invention, and are not always limited to one including all the described configurations.

Further, some configurations of a certain embodiment can be replaced with configurations of another embodiment, and configurations of another embodiment can be added to configurations of a certain embodiment. A part of the configurations of each of the embodiments can be added, removed, and replaced with the other configurations. For example, the cell culture apparatus of the third embodiment is constructed using the liquid feeder of the first embodiment, but it does not require stating that the cell culture apparatus can be constituted as the configuration which uses the liquid feeder of the second embodiment.

Furthermore, some of the configurations, the functions, the control part, and the like described above may be achieved with hardware obtained by design or the like of an integrated circuit and can be achieved with software by creating a program that achieves some or all of them.

LIST OF REFERENCE SIGNS 1, 16 liquid feeders
2 liquid bottle
3, 9, 21, 31, 43 air pressure adjustment pipes
4, 22 gas continuity valves
5, 23, 34 supply pipes
6 pump
7, 38 feed pipes
8 receptor
10, 30, 45, 54, 62 filters
11, 25 branch points
12, 27 gas introduction valves
13, 28 external air introduction valves
14, 29 gas bags
15, 65 controllers
17 liquid bag
18 cell culture apparatus
20 cell bag
22 gas continuity valve
24 opening/closing valve
26 ventilation branch point
32 check valve
33 culture medium bottle
35 supply valve
36 supply pump
37 third gas opening/closing valve
39 culture container
40 feeding port
41 air pressure adjustment port
42 discharge port
44 air pressure adjustment valve
46 discharge pipe
47 discharge control valve
48 discharge pump
49 drain pipe
50 drain bag
51 ventilation pipe
52 first gas opening/closing valve
53 second gas opening/closing valve
55 humidifying tube
56 humidifying bottle
57 humidifying tube
58 flow rate regulator
59 gas mixer
60 100% $CO_2$ cylinder
61 nitrogen cylinder 63 thermostatic chamber
64 refrigerator

The invention claimed is:

1. A liquid feeder comprising:
a receptor connected to one end of a feed pipe for feeding a liquid, the receptor receiving the liquid;
a gas bag connected to the other end of the feed pipe, for holding a gas for suppressing qualitative changes of the liquid;
a liquid feeding mechanism part for feeding by positioning the liquid between gas from the qas bag at both ends of the liquid to be fed to the receptor by the feed pipe;
a liquid bottle holding the liquid;
flow channels connecting the feed pipe to the liquid bottle; and
branch points connected to the flow channels connected to the gas bag,
wherein the liquid feeding mechanism part includes a pump placed in the feed pipe, and a gas introduction valve for introducing the gas of the gas bag to the branch point,
wherein when the branch point is provided above the liquid level of the liquid held in the liquid bottle, and
when the liquid in flow channels connected to the liquid bottle returns to the liquid bottle by dropping into the liquid bottle, the flow channels leading to the liquid bottle are filled with the gas.

2. The liquid feeder according to claim 1,
wherein the liquid feeding mechanism part further includes:
an air pressure adjustment pipe for connecting the liquid bottle to the gas bag; and
a gas continuity valve for controlling the opening and the closing of the air pressure adjustment pipe.

3. The liquid feeder according to claim 1, further comprising an air pressure adjustment pipe having a check valve and connected to the gas bag.

4. The cell culture apparatus which uses the liquid feeder according to claim 1,
wherein the receptor is a culture container for culturing cells, and the liquid is a liquid culture medium for culturing the cells.

5. The cell culture apparatus according to claim 4,
wherein the gas includes a predetermined concentration of $CO_2$ gas.

6. A liquid feeder comprising:
a receptor connected to one end of a feed pipe for feeding a liquid, the receptor receiving the liquid;
a gas bag connected to the other end of the feed pipe, for holding a gas for suppressing qualitative changes of the liquid;
a liquid feeding mechanism part for feeding by positioning the liquid between gas from the gas bag at both ends of the liquid to be fed to the receptor by the feed pipe;
a liquid bag for holding the liquid;
flow channels connecting the feed pipe to the liquid bag; and
branch points connected to the flow channels connected to the gas bag,
wherein the liquid feeding mechanism part includes a pump placed in the feed pipe, and a gas introduction valve for introducing the gas of the gas bag to the branch point,
wherein the branch point is provided above the liquid level of the liquid held in the liquid bag, and
when the liquid of the flow channels connected to the liquid bag returns to the liquid bag by dropping into the liquid bag, the flow channels leading to the liquid bag are filled with the gas.

7. A liquid feeder comprising:
a holding container for holding a liquid;
a receptor for receiving the liquid;
a liquid feeding mechanism part which uses a feed pipe to feed the liquid in the holding container to the receptor; and
a gas bag connected to the holding container, for holding the gas for suppressing qualitative changes of the liquid;
flow channels connecting the feed pipe to the holding container; and
branch points connected to the flow channels connected to the gas bag,
wherein the liquid feeding mechanism part holds the gas for suppressing qualitative changes of the liquid in a gas phase contacting the liquid in the holding container,
wherein the liquid feeding mechanism part includes a pump placed in the feed pipe, and a gas introduction valve for introducing the gas from the gas bag to the branch point, and
when the branch point is provided above the liquid level of the liquid held in the holding container and the liquid in the flow channels connected to the holding container returns to the holding container by dropping into the holding container, the flow channels leading to the holding container are filled with the gas for suppressing the qualitative changes of the liquid.

8. The liquid feeder according to claim 7,
wherein the liquid feeding mechanism part includes:
an air pressure adjustment pipe for connecting the holding container to the gas bag; and
a gas continuity valve for controlling the opening and the closing of the air pressure adjustment pipe.

9. The liquid feeder according to claim 7, comprising an air pressure adjustment pipe having a check valve and connected to the gas bag.

10. The cell culture apparatus which uses the liquid feeder according to claim 7,
wherein the receptor is a culture container for culturing cells, and the liquid is a liquid culture medium for culturing the cells.

11. The cell culture apparatus according to claim 7,
wherein the gas for suppressing qualitative changes of the liquid is a gas including a predetermined concentration of $CO_2$ gas.

* * * * *